United States Patent
Jawidzik

(10) Patent No.: US 11,464,565 B2
(45) Date of Patent: Oct. 11, 2022

(54) ELECTRONIC SHROUD FOR LASER EMISSION CONTROL

(71) Applicant: Alcon Inc., Fribourg (CH)

(72) Inventor: Geoffrey C. Jawidzik, Mission Viejo, CA (US)

(73) Assignee: Alcon Inc., Fribourg (CH)

( * ) Notice: Subject to any disclaimer, the term of this patent is extended or adjusted under 35 U.S.C. 154(b) by 56 days.

(21) Appl. No.: 17/089,896

(22) Filed: Nov. 5, 2020

(65) Prior Publication Data

US 2021/0137595 A1    May 13, 2021

Related U.S. Application Data

(60) Provisional application No. 62/934,605, filed on Nov. 13, 2019.

(51) Int. Cl.
| | |
|---|---|
| *A61B 18/20* | (2006.01) |
| *G01V 8/20* | (2006.01) |
| *A61B 17/00* | (2006.01) |

(52) U.S. Cl.
CPC .............. *A61B 18/20* (2013.01); *G01V 8/20* (2013.01); *A61B 2017/00973* (2013.01)

(58) Field of Classification Search
CPC ............ A61B 18/20; A61B 18/18; A61B 2017/00973; G01V 8/20
USPC ........................................ 606/1, 11
See application file for complete search history.

(56) References Cited

U.S. PATENT DOCUMENTS

| | | | |
|---|---|---|---|
| 5,098,426 A | * | 3/1992 | Sklar .................. A61F 9/008 606/4 |
| 6,659,998 B2 | | 12/2003 | Dehoogh et al. |
| 6,962,581 B2 | | 11/2005 | Thoe |
| 7,619,171 B2 | | 11/2009 | Horvath |
| 7,626,132 B2 | | 12/2009 | Mezhinsky |
| 8,308,716 B2 | | 11/2012 | Horvath |
| 8,465,473 B2 | | 6/2013 | Horvath |
| 8,680,412 B2 | | 3/2014 | Horvath |
| 10,864,054 B2 | | 12/2020 | Jochinsen et al. |
| 10,901,450 B2 | | 1/2021 | Jawidzik |
| 2008/0004608 A1 | | 1/2008 | Dacquay |
| 2015/0173725 A1 | | 6/2015 | Maxson |
| 2019/0239971 A1 | * | 8/2019 | Lim .................. B25J 13/04 |
| 2019/0354200 A1 | | 11/2019 | Rapoport |
| 2019/0354201 A1 | | 11/2019 | Rapoport |

* cited by examiner

*Primary Examiner* — Aaron F Roane

(57) ABSTRACT

Disclosed embodiments provide systems and methods for preventing unintentional laser emission via an integrated foot controller having an electronic shroud that is implemented using electronics and software. The risk of unintentional laser emission is reduced by permitting laser emission via the pedal of the foot controller only at defined stages of surgical procedures, and by requiring that the user initiate control of laser emission by actuating existing switches on the foot controller in a specified sequence, such as a passcode unique to a particular user. Additionally, disclosed embodiments include one more proximity sensors useful to detect data indicative of the presence of the user's foot on the foot controller. Such data may be useful in determining whether the system should remain in a ready state for laser emission or whether the system should be taken out of ready state to reduce the risk of unintentional laser emission when the user's foot is not present.

17 Claims, 5 Drawing Sheets

ELECTRONIC SHROUD FOR LASER EMISSION CONTROL

PRIORITY CLAIM

This application claims the benefit of priority of U.S. Provisional Patent Application Ser. No. 62/934,605 titled "ELECTRONIC SHROUD FOR LASER EMISSION CONTROL," filed on Nov. 13, 2019, whose inventor is Geoffrey C. Jawidzik, which is hereby incorporated by reference in its entirety as though fully and completely set forth herein.

DESCRIPTION OF THE RELATED ART

When surgically treating a patient, a surgeon generally uses a surgical system that requires the control of a variety of different pneumatic and electronically driven subsystems. Operation of the various subsystems is generally controlled by a processor driven console. The processor receives mechanical or electronic inputs from the surgeon or other medical professionals to control the operational characteristics of the various subsystems.

In ophthalmic surgical systems, primary control foot controllers connected to the console are generally used to control a variety of surgical subsystems. To control the surgical system and its associated handpieces during the various stages of the surgical procedure, the surgeon either instructs a nurse or other medical professionals to alter the machine settings on the surgical system, or uses the primary control foot controller to change such settings or activate a hand-piece. During certain ophthalmic surgical procedures, such as vitrectomies and certain retina surgeries, laser photocoagulation may be performed to cauterize blood vessels on the retina. During such procedures, laser emission is generally controlled (e.g., activated or deactivated) using a foot controller. For safety, the regulatory standard requires that any foot-operated laser emission control switch be shrouded to prevent unintentional activation of the laser.

Typically, the shrouding of a laser emission control foot controller is accomplished by providing a physical enclosure over a stand-alone laser emission control foot controller that nonetheless permits a user to insert his or her foot from one direction, to be able actuate the foot controller by pressing downward. Other laser emission control foot controllers incorporate a moveable cover into the heel-region of the base of an otherwise non-laser emission control foot controller, which can be lifted up by the user using the toe region of their foot, to gain access to a button for a laser emission control switch. When lifted, the cover physically encloses the laser emission control switch. More recently, shrouding has been accomplished in an integrated foot controller with a large, fixed physical shroud incorporated onto a primary, multi-function foot controller, and laser emission control is performed using the pedal of that foot controller.

Each of these conventional laser emission foot controllers are problematic. Stand-alone laser emission control foot controllers with static enclosures occupy additional surgical floor space and stowage space and require that the user entirely relocate the foot from the primary, multi-function foot controller to the stand-alone laser emission foot controller. Moveable cover laser emission foot controllers may require that the user substantially reposition the foot and perform the unusual action of lifting a cover with the foot. The physical shroud of the integrated foot controllers is very bulky, which may be problematic for stowage.

Therefore, there is a need for an improved integrated foot controller, which reliably reduces the risk of unintentional operation of laser emission without requiring use of a secondary foot controller, incorporation of additional mechanical parts, or an increase in size of the foot controller.

BRIEF SUMMARY

The present disclosure relates generally to devices and methods for controlling a surgical system, and more particularly, to an integrated surgical foot controller with an electronic shroud that addresses the risk of unintentional laser emission.

In one embodiment, a foot controller coupled to a surgical console is disclosed. The foot controller coupled to the surgical console includes a base and a body coupled to the base. The body includes a plurality of switches configured to be actuated by a user in a defined sequence to enter a passcode to perform one or more actions of a surgical procedure.

In another embodiment, a method for controlling laser emission is disclosed. The method includes initiating a surgical procedure having one or more stages on a surgical console, at least one of the one or more stages being a laser stage, the laser stage comprising a laser emission state, selecting the laser stage, activating the laser ready state of the laser stage by entering a passcode using a foot controller coupled to the surgical console; and emitting a laser using the foot controller.

In yet another embodiment, a surgical system is disclosed. The surgical system includes a foot controller and a surgical console coupled to the foot controller. The surgical console includes a processor, and a memory having instructions stored thereon. When the instructions are executed by the processor, the processor performs an operation for controlling laser emission. The operation includes displaying one or more stages of a surgical procedure on the surgical console, at least one of the one or more stages being a laser stage, receiving user input, the user input indicating selection of the laser stage from the one or more stages of the surgical procedure, entering the laser stage, activating a laser ready state of the laser stage upon receiving a passcode entered by a user using the foot controller coupled to the surgical console, and emitting a laser when triggered by the user using the foot controller.

The following description and the related drawings set forth in detail certain illustrative features of one or more embodiments.

BRIEF DESCRIPTION OF THE DRAWINGS

The appended figures depict certain aspects of one or more disclosed embodiments and are therefore not to be considered limiting of the scope of this disclosure.

To facilitate understanding, identical reference numerals have been used, where possible, to designate identical elements that are common to the drawings. It is contemplated that elements and features of one embodiment may be beneficially incorporated in other embodiments without further recitation.

DETAILED DESCRIPTION

Embodiments disclosed herein provide systems and methods for reducing the risk of unintentional laser emission via an integrated foot controller having an electronic shroud that is implemented using electronics and software. The risk of unintentional laser emission is reduced by permitting laser emission via the pedal of the foot controller only at defined stages of surgical procedures, and additionally by requiring that the user initiate control of laser emission by actuating existing switches on the foot controller in a specified sequence, such as a passcode that is unlikely to be entered accidentally. Additionally, disclosed embodiments include one more proximity sensors useful to detect data indicative of the presence of the user's foot on the foot controller. Such data may further be useful in determining whether the system should remain in a ready state for laser emission or whether the system should be taken out of the ready state to reduce the risk of unintentional laser emission when the user's foot is not present.

Figure 1:
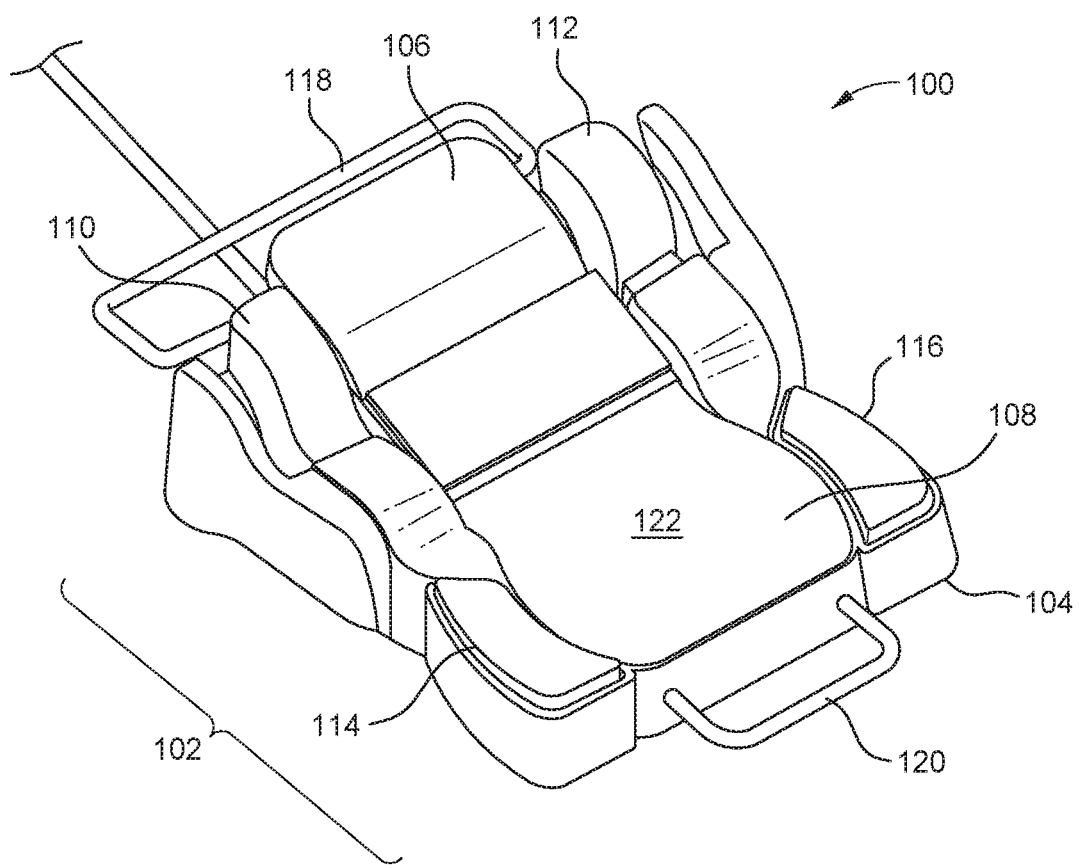
FIG. 1 illustrates a perspective view of a foot controller, in accordance with certain embodiments of the present disclosure.

FIG. 1 illustrates a perspective view of a foot controller 100, in accordance with certain embodiments of the present disclosure. The foot controller 100 includes a body 102 with a base 104 that supports the foot controller 100 on the operating room floor. The body 102 includes a footpedal 106, a heel rest 108, a left toe switch 110, a right toe switch 112, a left heel switch 114, and a right heel switch 116. A first handle 118 and a second handle 120 are coupled to the body 102. The configuration of switches, handles, and footpedals of FIG. 1 is included as an example. It is contemplated, however, that the foot controller 100 may have any suitable number and configuration of switches, handles, and footpedals, which are configured to be actuated by a user in a defined sequence to enter a passcode to perform one or more actions of a surgical procedure.

The surgeon uses footpedal 106 for proportional control of certain functions or surgical parameters during a surgical procedure. For example, the surgeon depresses the footpedal 106 using the distal portion of his or her foot to move from a fully undepressed to, for example, a fully depressed position in which the footpedal 106 lies in generally the same plane as the heel rest 108.

The left toe switch 110 and the right toe switch 112 are generally dual mode binary switches that can be vertically or horizontally actuated to control certain functions or surgical parameters. For example, the first mode is actuated when a surgeon presses downward on the left toe switch 110 or the right toe switch 112. The second mode is actuated when the surgeon presses in a generally outward, horizontal direction on the left toe switch 110 or the right toe switch 112 with the side of his or her foot. The left heel switch 114 and right heel switch 116 are generally binary switches that are actuated when a surgeon presses downward with his or her heel.

As discussed in more detail below, the foot controller 100 is useful as an integrated primary control foot controller and laser emission control foot controller when physically or wirelessly coupled to a surgical console.

Figure 2:
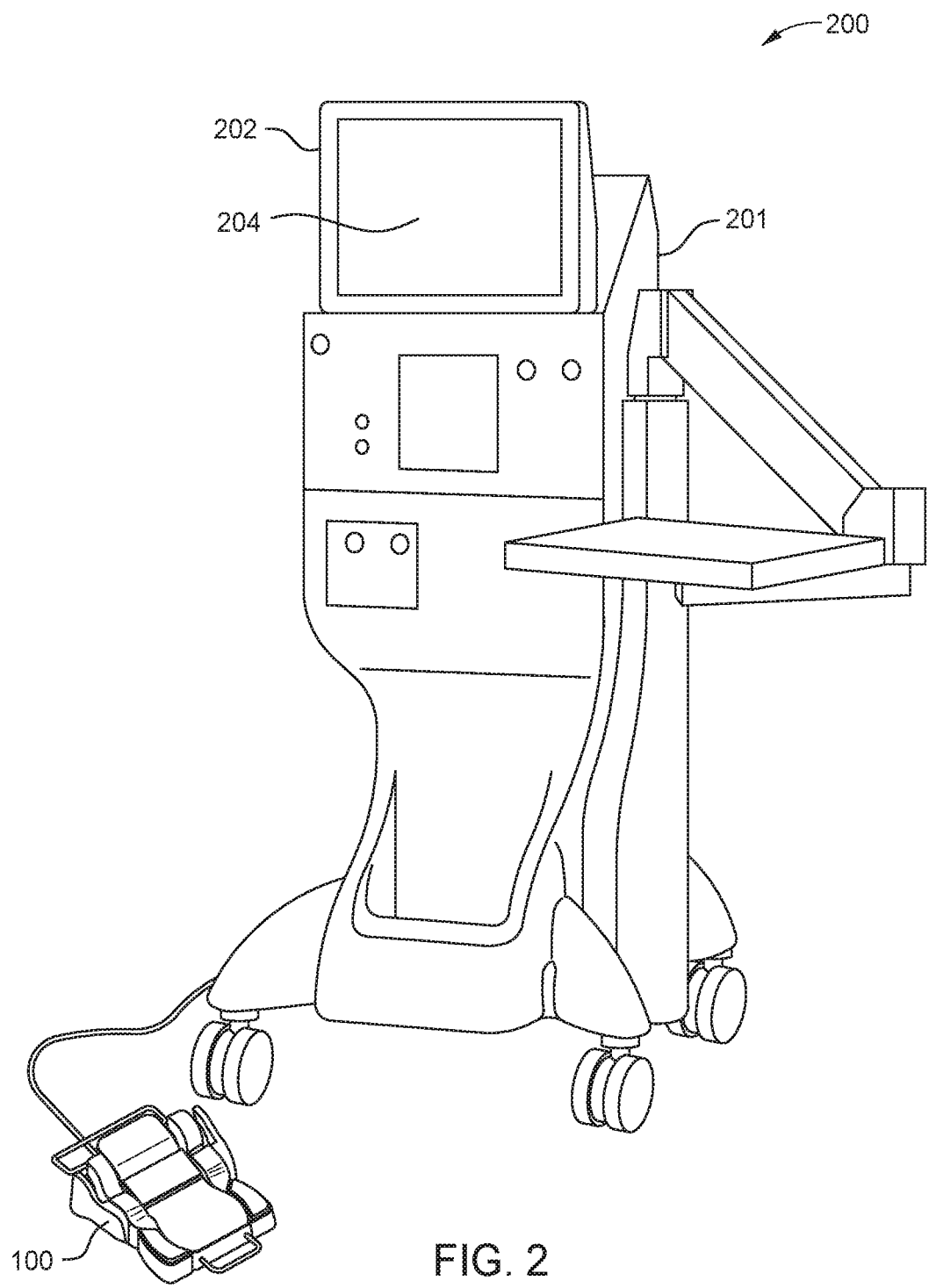
FIG. 2 illustrates a perspective view of a surgical system including a surgical console having a foot controller coupled thereto, in accordance with certain embodiments of the present disclosure.

FIG. 2 illustrates a perspective view of a surgical system 200 including a surgical console 201 operably coupled, physically or wirelessly, to any number of user interfaces, including a foot controller 100, in accordance with certain embodiments of the present disclosure. The surgical console 201 allows a user, generally a surgeon or other medical professional, to begin a surgical procedure by setting the initial operating parameters and modes into the surgical console 201, for example by using an electronic display screen 202 (e.g., via a touch-screen interface, mouse, trackball, keyboard, etc.), which includes a graphical user interface (GUI) 204. The electronic display screen 202 allows the user to access various menus and screens related to the functions and operations of the surgical console 201. The electronic display screen 202 is controlled by a processor coupled to a memory (e.g., random access memory (RAM)). The instructions stored in the memory configure the processor to execute one or more operations, such as displaying the various menus and screens on electronic display screen 202 as well as the other operations described herein. For example, as the user advances through the surgical procedure, user input regarding changes to the operating modes and parameters is received by the processor, which executes instructions stored in memory based on that input and controls the electronic display screen 202.

As discussed above, one or more users, generally a surgeon or another medical professional, interacts with the graphical user interface 204 throughout the various stages of the surgical procedure. For example, the user, or another medical professional in the operating room, may toggle from one stage of the procedure to the next by selecting the next stage on the graphical user interface 204. The user may also toggle to the next stage using one or more of the left toe switch 110, the right toe switch 112, the left heel switch 114, or the right heel switch 116 of the foot controller 100. During certain surgical procedures, such as vitrectomy, one such stage is a laser photocoagulation stage ("laser stage") during which a laser is used to treat the patient, for example to reattach the retina of the patient. Only upon entering this stage is it possible to enable laser emission control, by pressing or otherwise actuating toe switches in a defined sequence.

During the laser stage of the surgical procedure, the surgical console 201 may generally be placed in a ready state or a laser emission state. The surgical console 201 may be automatically placed in a ready state when it enters the laser stage or the surgical console 201 may be put into a ready state by a user, such as the surgeon or another medical professional. In the ready state, the surgical console 201 is awaiting input needed to enter the laser emission state. In the laser emission state, the laser is emitted when the user presses the footpedal 106. According to embodiments of the present disclosure, the foot controller 100 is used to place the surgical console 201 in the laser emission state. For example, the user enters a passcode, which is generally any suitable sequence of actuations of the various switches of the foot controller 100. For example, the user may enter a passcode by actuating the left toe switch 110 and the right toe switch 112 by pressing, for example, right-horizontal, left-horizontal, right-horizontal. It is contemplated that the user may be permitted to define the passcode sequence, or select from pre-defined sequences, provided the sequence meets a required level of intentionality to ensure safety by minimizing the risk of unintentional input. It is also contemplated that when the passcode is entered and laser emission control is enabled, an audible or tactile signal is generated, to alert the user.

Once the user has entered the passcode, the surgical console 201 enters the laser emission state and the user may press down on the footpedal 106 to emit the laser as needed for the surgical procedure.

This passcode, therefore, functions as an electronic shroud because it minimizes the risk of unintentional activation of the laser since the laser is only emittable once the user has affirmatively entered a defined, adequately complex passcode. Thus, the foot controller 100 serves as an integrated foot controller that allows for the switches and pedal to be used to step through the various stages of the surgical procedure and to be used to control various handheld surgical devices, such as a laser probe used for photocoagulation.

As shown in FIG. 1, the foot controller 100 may also include one or more sensors 122. A single sensor 122 disposed on the heel rest 108 is shown as an example. The one or more sensors 122 are generally any sensor capable of collecting data to indicate whether the user's foot is on, or within a predetermined distance from, the footpedal 106. Suitable sensors include, but are not limited to, photosensors and photodiodes positioned to reliably sense the presence of a human foot. In some examples, the one or more sensors 122 include a photodiode, which emits light, and a photosensor, which detects light, that work in conjunction to determine when the user's foot is present. The photodiode may be coupled to the left side of the foot controller 100 and the photosensor may be coupled to the right side of the foot controller 100, such as the photodiode being coupled to the left toe switch 110 and the photosensor being coupled to the right toe switch 112. In another example, the one or more sensors 122 are reflective-type photodetectors located in the surface of the foot controller 100 where the user places his or her heel, such as in the heel rest 108.

In operation, the data provided by the one or more sensors 122 is used to determine whether the user's foot is on the footpedal 106, or within a predetermined distance from the footpedal 106. If the data from the one or more sensors 122 indicates the user's foot is on the footpedal 106 or within the predetermined distance from the footpedal 106, it is presumed the foot present is that of the user who entered the passcode and the system remains in the ready state or the laser emission state such that the user can readily emit the laser. If the data signifies that the user's foot is not on the footpedal 106, or within the predetermined distance from the footpedal 106, then the system is generally taken out of ready state or the laser emission state, to reduce the risk of unintentional laser emission. The data collected from the one or more sensors 122 and communicated to the surgical console 201 therefore provides another form of electronic shrouding to further reduce the risk of unintentional laser emission. This data also provides a time out feature by which the system is taken out of the ready state or the laser emission state after a certain, predetermined period of time during which the user's foot is not on the footpedal 106 or within the predetermined distance from the footpedal 106.

It is further contemplated that embodiments of the electronic shroud disclosed herein are combinable with other means of risk mitigation, to enhance safety further. For example, in further embodiments, the foot controller 100 includes additional design features, which are useful for further minimizing the risk of inadvertent emission of the laser. For example, the body 102 of the foot controller 100 may be designed in a dam-like, or otherwise recessed, manner to protect the footpedal 106 from being unintentionally pressed.

Figure 3:
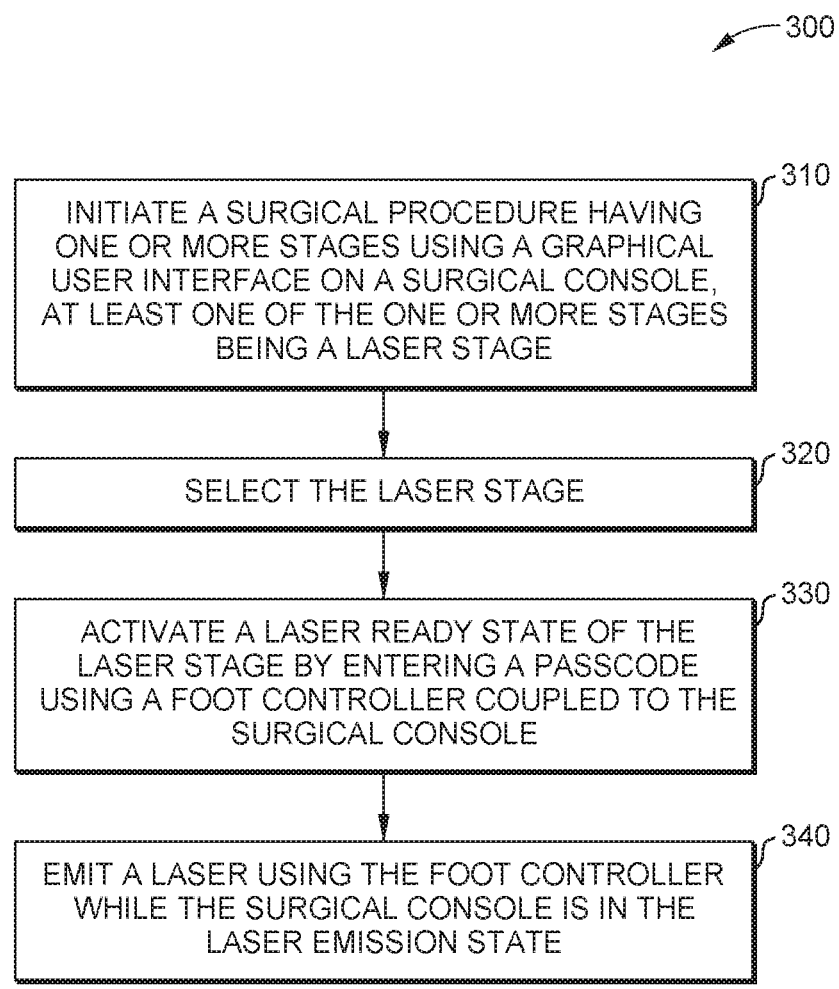
FIG. 3 is a flow diagram illustrating a method for controlling a laser, in accordance with certain embodiments of the present disclosure.

FIG. 3 is a flow diagram illustrating a method 300 in accordance with certain embodiments of the present disclosure. The method 300 is useful for controlling surgical equipment with the foot controller 100 of FIGS. 1-2, as an example. However, the present disclosure contemplates that the method 300 is useful for controlling any suitable foot controller.

The method 300 begins with initiating a surgical procedure having one or more stages using a graphical user interface on a surgical console, such as surgical console 201, at operation 310. At least one of the one or more stages is a laser stage. At operation 320, the laser stage is selected. For example, a nurse may select the laser stage on the graphical user interface of the surgical console or the surgeon may select the laser stage by toggling to the laser stage using a foot controller. At operation 330, the laser emission state of the laser stage is triggered by entering a passcode using a foot controller, such as the foot controller 100, coupled to a surgical console, such as the surgical console 201.

In one embodiment, the laser stage is first selected by a medical professional, such as a nurse. Second, the medical professional, such as the nurse, affirmatively puts the surgical system 200 in the laser standby state using the graphical user interface 204. Third, the surgeon enters the passcode, which initiates the laser ready state of the laser stage such that the surgeon can emit the laser as desired.

In another embodiment, the laser stage is first selected by the medical professional, such as the nurse, using the graphical user interface 204 and the surgical system 200 is then automatically placed in the laser standby state. Then the surgeon enters the passcode, which puts the surgical system 200 in the laser ready state such that the surgeon can emit the laser as desired. In other words, in this embodiment, the laser stage is automatically in the standby state and no separate, affirmative action of the medical is needed to trigger the ready state.

At operation 340, a laser is emitted using the foot controller while the surgical console is in the laser ready state. The emission of the laser using the foot controller is repeatable any number of times needed for the surgical procedure so long as the foot controller is in the laser ready state. At the conclusion of the method 300, the user may select the next stage of the surgical procedure using the graphical user interface or the foot controller to continue surgically treating the patient.

Figure 4:
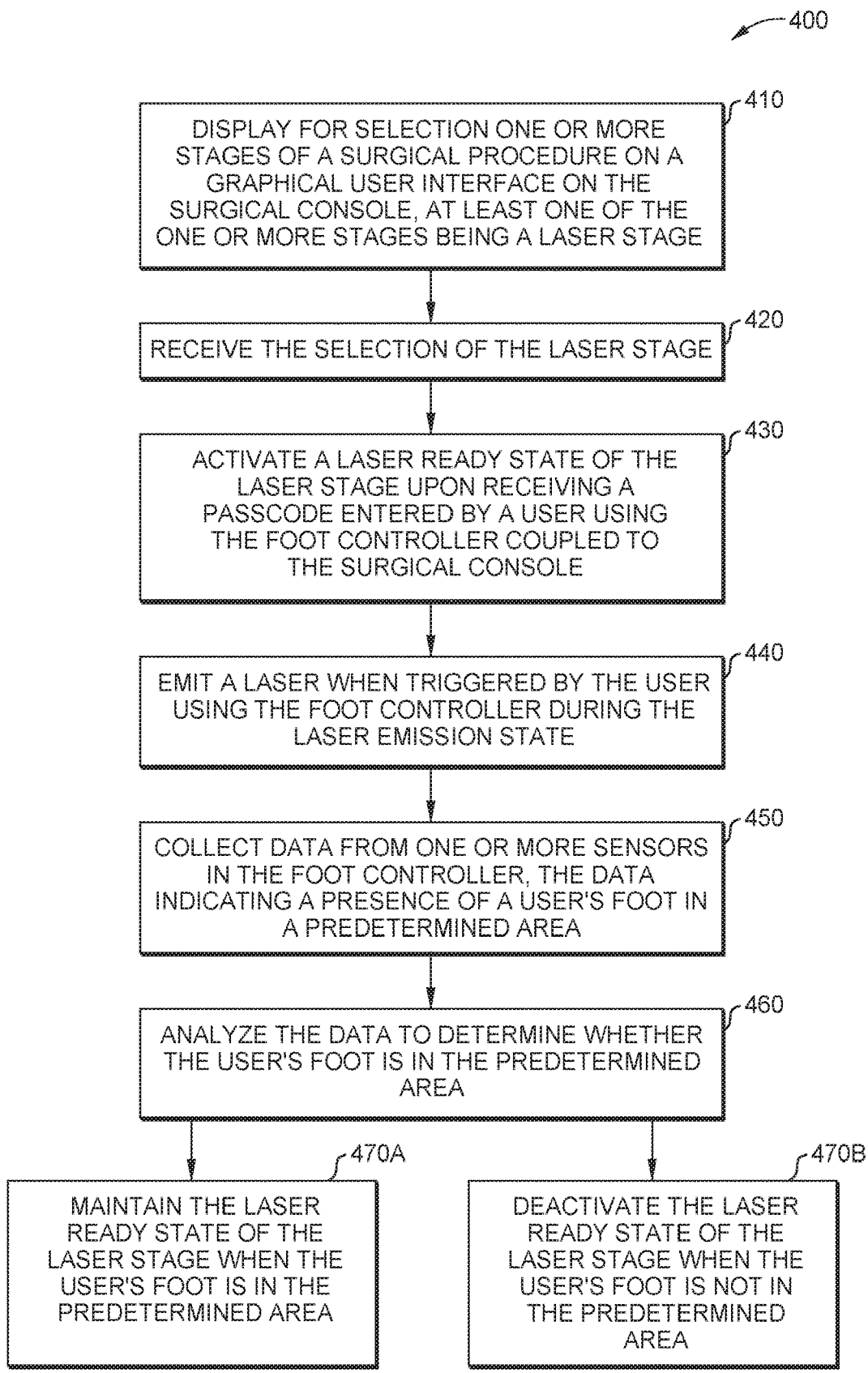
FIG. 4 is a flow diagram illustrating a method for controlling a laser, in accordance with certain embodiments of the present disclosure.

As shown in FIG. 4, a method 400 begins at operation 410 with displaying for selection one or more stages of a surgical procedure on a graphical user interface of a surgical console. At least one of the one or more stages is a laser stage. At operation 420, the selection of the laser stage is received. The laser emission state of the laser stage is activated by receiving a passcode entered by a user using a foot controller coupled to the surgical console at operation 430. At operation 440, a laser is emitted after triggering by the user using the foot controller during the laser emission state.

At operation 450, data is collected from one or more sensors in the foot controller. The data is indicative of a presence of a user's foot on the footpedal of the foot controller or within a predetermined distance from the foot controller. The data is analyzed to determine whether the user's foot is in the predetermined area at operation 460. If the data from the one or more sensors indicates the user's foot is on the footpedal or within the predetermined distance from the footpedal, it is presumed the foot present is that of the user who entered the passcode and the system remains in the laser ready state such that the user can readily emit the laser at operation 470A. If the data signifies that the user's foot is not on the footpedal, or within the predetermined distance from the footpedal, then the system is generally taken out of the laser emission state, to reduce the risk of unintentional laser emission at operation 470B. The method 400 is generally performed using a processor and a memory having instructions stored thereon, which when executed by the processor performs the operations of the method 400, or using a custom electronic circuit.

Through the inclusion of these several electronic shrouding measures disclosed herein, the emission of the laser is reliably restricted to intentional acts of the user with high confidence. The disclosed embodiments allow the surgeon to place a laser in the laser emission state and then continue to fire the laser in the laser emission state using the integrated foot controller.

Figure 5:
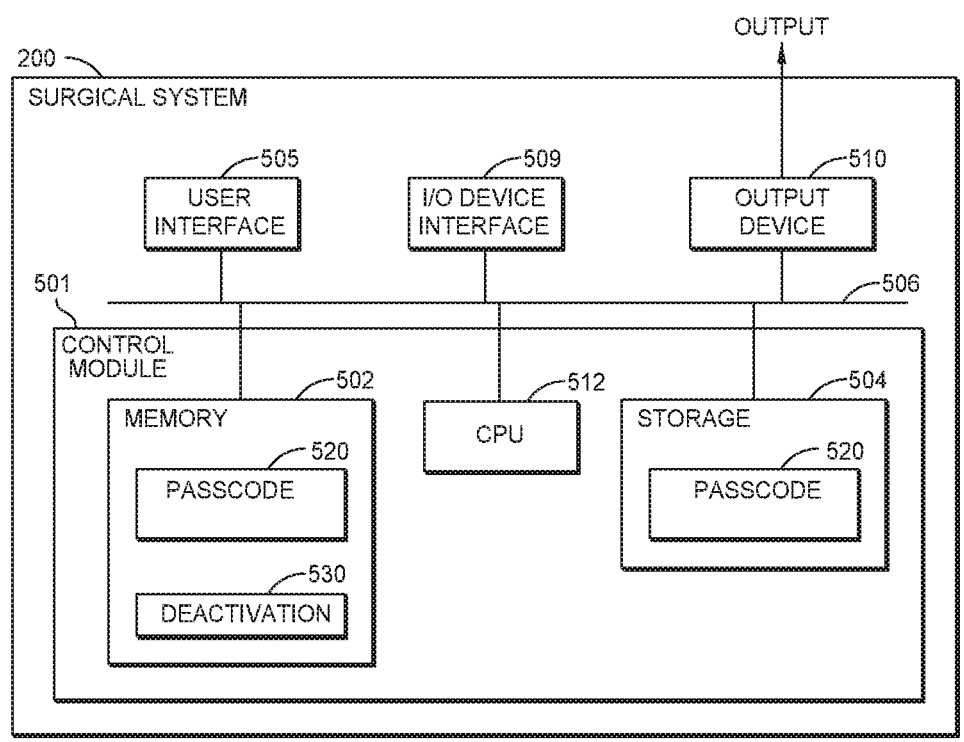
FIG. 5 illustrates exemplary components of the surgical system of FIG. 2, in accordance with certain embodiments of the present disclosure.

Embodiments of the present disclosure beneficially provide electronic shrouding from unintentional activation of the laser in a reliable manner that interferes minimally with the overall use of the system of which it is a part using a processor and memory within a controller of the surgical console, as shown in FIG. 5, which illustrates exemplary components of the surgical system of FIG. 2, in accordance with certain embodiments.

FIG. 5 illustrates an exemplary diagram showing how various components of the surgical system 200 of FIG. 2 communicate and operate together. As shown, surgical system 200 includes, without limitation, control module 501, user interface 505, an interconnect 506, output device 510, and at least one Input/Output (I/O) device interface 509, which may allow for the connection of various I/O devices (e.g., keyboards, displays, mouse devices, pen input, etc.) to surgical system 200.

Control module 501 includes a processor or central processing unit (CPU) 512, a memory 502, and storage 504. CPU 512 may retrieve and execute programming instructions stored in the memory 502. Similarly, CPU 512 may retrieve and store application data residing in memory 502. Interconnect 506 transmits programming instructions and application data, among CPU 512, I/O device interface 509, user interface 505, memory 502, storage 504, output device 510, etc. CPU 512 can represent a single CPU, multiple CPUs, a single CPU having multiple processing cores, and the like. Additionally, memory 502 represents random access memory. Furthermore, the storage 504 may be a disk drive. Although shown as a single unit, storage 504 may be a combination of fixed or removable storage devices, such as fixed disc drives, removable memory cards or optical storage, network attached storage (NAS), or a storage area-network (SAN).

Memory 502 includes instructions, which when executed by the processor, performs an operation for controlling laser emission, as described in the embodiments herein. For example, according to embodiments described herein, a passcode 520 for activating a laser emission state of a laser stage of a surgical procedure is stored in storage 504. In certain embodiments, passcode 520 is configured by the manufacturer. In certain other embodiments, passcode 520 is user-defined, meaning that a user is able to define the sequence of switches that need to be pressed for the activation of the laser emission state. In certain other embodiments, surgical system 200 may be configured with a passcode and also allow a user to define a second passcode as well.

Once a medical professional selects the laser stage, then passcode 520 is retrieved from the storage 504. The surgical system 200 is then configured by instructions in the memory 502 to stand by until a passcode that matches passcode 520 is entered. In operation, then the user enters a passcode, which is cross-referenced with the passcode 520. Upon verification of the passcode, the memory 502 executes instructions to allow for surgical system 200 to enter the laser ready state, which allows a laser to be emitted once the footpedal is pressed by the user. The memory 502 may also include deactivation instructions 530, which comprises executable instructions for deactivating or maintaining the laser emission state based on information received from one or more sensors, according to embodiments described herein.

As shown, surgical system 200 also includes output device 510. As described above, in some embodiments, surgical system 200 emits a laser from output device 510. In one example, output device 510 may be a pneumatic or hydraulic output device that dispenses a laser beam.

The disclosed embodiments do not require use of a secondary foot controller. Nor do the disclosed embodiments require incorporation of additional mechanical parts. Embodiments of the present disclosure therefore provide improved accessibility of all foot controller controls and reduced size, which is especially beneficial during stowage of the foot controller.

While the embodiments disclosed herein are described in the context of shrouded lasers for ophthalmic procedures as an example, it is also contemplated that the electronic shrouding is useful for additional procedures and medical devices for which inadvertent activation is dangerous and undesirable.

The foregoing description is provided to enable any person skilled in the art to practice the various embodiments described herein. Various modifications to these embodiments will be readily apparent to those skilled in the art, and the generic principles defined herein may be applied to other embodiments. Thus, the claims are not intended to be limited to the embodiments shown herein, but are to be accorded the full scope consistent with the language of the claims.

What is claimed is:

1. A foot controller coupled to a surgical console, comprising:
    a base; and
    a body coupled to the base, the body comprising:
        a plurality of switches configured to be actuated by a user in a defined sequence to enter a passcode to perform one or more actions of a surgical procedure; and
        one or more sensors disposed on or in contact with one or more of the plurality of switches, wherein the one or more sensors are configured to detect a presence of a user's foot;
        wherein the plurality of switches comprise:
            a left toe switch;
            a right toe switch;
            a left heel switch
            a right heel switch;
            a foot pedal disposed between the left toe switch and the right toe switch; and
            a heel rest coupled to the foot pedal and disposed between the left heel switch and the right heel switch;
        wherein the one or more sensors comprise a photodiode and a photosensor configured to work in conjunction to detect the presence of the user's foot.

2. The foot controller of claim 1, wherein the one or more actions comprise putting the surgical console in a laser ready state of a laser stage of the surgical procedure.

3. The foot controller of claim 2, wherein actuating one or more of the plurality of switches after entering the passcode causes the surgical console to emit a laser beam.

4. The foot controller of claim 1, wherein the one or more sensors comprise a single sensor disposed on or in contact with the heel rest.

5. The foot controller of claim 1, wherein the photodiode is coupled to the left toe switch and the photosensor is coupled to the right, toe switch.

6. A method for controlling laser emission, comprising:
initiating a surgical procedure having one or more stages on a surgical console, at least one of the one or more stages being a laser stage, the laser stage comprising a laser ready state;
selecting the laser stage;
activating the laser ready state of the laser stage by entering a passcode using a foot controller coupled to the surgical console; and
emitting a laser using the foot controller.

7. The method of claim 6, wherein selecting the laser stage comprises selecting the laser stage from the one or more stages using a graphical user interface or toggling to the laser stage using the foot controller.

8. The method of claim 6, wherein entering the passcode using the foot controller comprises depressing one or more switches on the foot controller in a defined. sequence.

9. The method of claim 6, wherein the passcode is sequence of actuations of various switches on the foot controller.

10. The method of claim 6, further comprising:
collecting data from one or more sensors disposed in the foot controller, the data indicating a presence of a user's foot in a predetermined area.

11. The method of claim 10, further comprising:
deactivating the laser emission state of the laser stage when the collected data indicates the user's foot is not in the predetermined area.

12. A surgical system, comprising:
a foot controller; and
a surgical console coupled to the foot controller, the surgical console comprising:
a processor; and
a memory having instructions stored thereon, which when executed by the processor, cause the processor to perform an operation for controlling laser emission, the operation comprising:
displaying one or more stages of a surgical procedure on the surgical console, at least one of the one or more stages being a laser stage;
receiving user input, the user input indicating selection of the laser stage from the one or more stages of the surgical procedure;
entering the laser stage;
activating a laser ready state of the laser stage upon receiving a passcode entered by a user using the foot controller coupled to the surgical console; and
emitting a laser whenriggered by the user using the foot controller.

13. The surgical system of claim 12, wherein the operation further comprises:
receiving data collected from one or more sensors in the foot controller, the data indicating a presence of a user's foot in a predetermined area; and
analyzing the data to determine whether the user's foot is in the predetermined area.

14. The surgical system of claim 13, wherein the operation further comprises:
deactivating the laser ready state of the laser stage when the analyzed data indicates the user's foot is not in the predetermined area.

15. The surgical system of claim 13, wherein the operation further comprises:
maintaining the laser ready state of the laser stage when the analyzed data indicates the user's foot is in the predetermined area.

16. The surgical system of claim 12, wherein the foot controller comprises:
a base;
a body coupled to the base, the body comprising:
a left toe switch;
a right toe switch;
a left heel switch;
a right heel switch;
a foot pedal disposed between the left toe switch and the right toe switch; and
a heel rest coupled to the foot pedal and disposed between the left heel switch and the right heel switch;
one or more handles coupled to the body; and
one or more sensors disposed on or in contact with one or more of the foot pedal, the heel rest, the left toe switch, the right toe switch, the left heel switch, or the right heel switch.

17. The surgical system of claim 16, wherein the one or more sensors are configured to detect a presence of a user's foot.

* * * * *